United States Patent
Antel et al.

(10) Patent No.: US 8,486,710 B2
(45) Date of Patent: Jul. 16, 2013

(54) METHOD, SENSOR AND SYSTEM FOR MEASURING A LOWER HEATING VALUE AND A WOBBE INDEX OF A GASEOUS FUEL

(75) Inventors: William Joseph Antel, München-Eching (DE); Nirm Velumylum Nirmalan, Niskayuna, NY (US); Stephen Adam Solovitz, Croton on Hudson, NY (US); Nishant Vats, Jharkhand (IN); Subhrajit Dey, Karnataka (IN); Robert Michael Orenstein, Atlanta, GA (US); Matthew Moorman, Albuquerque, NM (US); Ronald P. Manginell, Albuquerque, NM (US)

(73) Assignee: General Electric Company, Nisakayuna, NY (US)

( * ) Notice: Subject to any disclaimer, the term of this patent is extended or adjusted under 35 U.S.C. 154(b) by 2446 days.

(21) Appl. No.: 11/299,588

(22) Filed: Dec. 12, 2005

(65) Prior Publication Data

US 2007/0089485 A1    Apr. 26, 2007

Related U.S. Application Data

(60) Provisional application No. 60/722,331, filed on Sep. 30, 2005.

(51) Int. Cl.
*G01N 33/00* (2006.01)
(52) U.S. Cl.
USPC .......................................................... 436/143
(58) Field of Classification Search
USPC .......................................................... 436/143
See application file for complete search history.

(56) References Cited

U.S. PATENT DOCUMENTS

| | | | |
|---|---|---|---|
| 4,329,874 A | | 5/1982 | Maeda |
| 5,288,149 A | * | 2/1994 | Meyer .............................. 374/36 |
| 5,807,749 A | * | 9/1998 | Hornemann ................... 436/143 |
| 5,834,627 A | | 11/1998 | Ricco et al. |
| 6,517,237 B1 | * | 2/2003 | Hammond et al. ............. 374/31 |
| 6,786,716 B1 | | 9/2004 | Gardner et al. |

FOREIGN PATENT DOCUMENTS

| | | |
|---|---|---|
| WO | WO8502908 | 7/1985 |
| WO | WO03048692 A1 | 6/2003 |

OTHER PUBLICATIONS

EPO Search Report dated Jan. 10, 2007.
M. Seto, H. Muto and Y. Kajio; 1995 International Gas Research Conference; "Development of Calorie Transmitter for Quick Response Calorific Value Control"; 10 pages. Dr. R. Heb and Dr. D. Altemark; 1996 International Gas Research Conference; "Flameless System for the Measurement of the Gross Calorific Value and the Wobbe Number of Fuel Gases"; 11 pages.

* cited by examiner

*Primary Examiner* — Michael Marcheschi
*Assistant Examiner* — Jonathan Hurst
(74) *Attorney, Agent, or Firm* — Ann M. Agosti

(57) ABSTRACT

A method for measuring a lower heating value of a gaseous fuel. The method includes mixing a gaseous fuel with air to provide a combustible air-fuel mixture. The air-fuel mixture is directed to flow across a flow surface of a first micro-hotplate maintained at a constant temperature. A change in power required to maintain a constant temperature of the first micro-hotplate flow surface due to a convective and conductive heat transfer from the first micro-hotplate flow surface to the air-fuel mixture is measured. The air-fuel mixture is directed to flow across a flow surface of a second micro-hotplate maintained at a constant temperature. The air-fuel mixture is combusted as the air-fuel mixture flows across the second micro-hotplate flow surface. A change in power required to maintain a constant temperature of the second micro-hotplate flow surface due to the combustion of the air-fuel mixture is measured.

19 Claims, 2 Drawing Sheets

METHOD, SENSOR AND SYSTEM FOR MEASURING A LOWER HEATING VALUE AND A WOBBE INDEX OF A GASEOUS FUEL

CROSS REFERENCE TO RELATED APPLICATIONS

This application claims the benefit of U.S. Provisional Application No. 60/722,331, filed Sep. 30, 2005, which is hereby incorporated by reference in its entirety.

STATEMENT REGARDING FEDERALLY SPONSORED RESEARCH & DEVELOPMENT

The U.S. Government may have certain rights in this invention pursuant to contract number DE-FC26-63NT41448.

BACKGROUND OF THE INVENTION

This invention relates generally to monitoring gas turbine engine performance and, more particularly, to a method and system for measuring a lower heating value and Wobbe Index for a gaseous fuel.

A demand is increasing for gas-fired combustion turbines and reciprocating engines that can be reliably operated on Liquefied Natural Gas (LNG) or blends of pipeline natural gas and LNG, as well as a wide variety of low BTU gaseous fuels. Thus, there is need for a rapid and inexpensive method and system to determine a lower heating value (LHV) and/or a Wobbe Index of these fuels in order to ensure that engine performance is properly matched to the fuel characteristics.

Existing methods for determining the LHV and/or the Wobbe Index of a gaseous fuel include the use of a gas chromatograph (GC) system having a glass capillary system to separate the fuel constituents and a thermal conductivity detector (TCD) and/or a flame ionization detector (FID) to quantitatively identify the constituents. However, conventional GC systems have several drawbacks. GC systems are relatively expensive, typically costing about US$20,000.00 or more. Additionally, GC systems are difficult to operate, requiring significant training. Further, GC response is relatively slow, in that analysis times of several minutes are normally required.

Another method for determining the LHV and/or the Wobbe Index of a gaseous fuel is based on a correlation existing between the Wobbe Index and the density and dynamic viscosity of the fuel. Yet another method includes using a calorimeter to obtain a measure of fuel quality. For example, it is possible to exploit the correlation between thermal conductivity of the fuel gas and the heating value. This correlation exists for typical natural gas that is composed mostly of methane. However, problems with measurement accuracy may develop as fuel compositions vary.

The Wobbe Index (W) is a commonly used measurement of fuel quality that is given by the following equation:

$$W = \frac{LHV}{\sqrt{SG}} \quad \text{(Eq. 1)}$$

wherein SG is the specific gravity of the fuel being measured. Using this correlation, a Wobbe Index of a wide range of fuels can be measured. However, there is a drawback to this method. The correlation does not hold if there is a high concentration of some gases, such as $H_2$, $CO_2$ and/or LPG.

BRIEF DESCRIPTION OF THE INVENTION

In one aspect, the present invention provides a method for measuring a lower heating value of a gaseous fuel. The method includes mixing a gaseous fuel with air to provide a combustible air-fuel mixture. The air-fuel mixture is directed to flow across a flow surface of a first micro-hotplate maintained at a constant temperature. A change in power required to maintain a constant temperature of the first micro-hotplate flow surface due to a convective and conductive heat transfer from the first micro-hotplate flow surface to the air-fuel mixture is measured. The air-fuel mixture is directed to flow across a flow surface of a second micro-hotplate maintained at a constant temperature. The air-fuel mixture is combusted as the air-fuel mixture flows across the second micro-hotplate flow surface. A change in power required to maintain a constant temperature of the second micro-hotplate flow surface due to the combustion of the air-fuel mixture is measured.

In another aspect, the present invention provides a sensor for measuring a lower heating value of a gaseous fuel. The sensor includes an enclosure defining a chamber. The chamber is in flow communication with an air-fuel mixture supply line configured to supply a combustible air-fuel mixture to the chamber. A first micro-hotplate is positioned within the chamber and includes at least one flow surface. The at least one flow surface is configured to contact the air-fuel mixture flowing through the chamber. A second micro-hotplate is positioned within the chamber and with respect to the first micro-hotplate. The second micro-hotplate includes at least one flow surface coated with a catalytic coating material configured to initiate combustion of the air-fuel mixture. A sensor exhaust is in flow communication with the chamber.

In another aspect, the present invention provides a system for measuring a lower heating value of a gaseous fuel. The system includes a flow control device configured to control at least one of a flow rate of air and a flow rate of a gaseous fuel for providing a combustible air-fuel mixture. A sensor is in flow communication with the flow control device. The sensor includes a first micro-hotplate having at least one flow surface. The first micro-hotplate is configured to measure convective and conductive heat losses from the first micro-hotplate to the air-fuel mixture flowing across the at least one flow surface. A second micro-hotplate is positioned with respect to the first micro-hotplate. The second micro-hotplate includes at least one flow surface coated with a catalytic coating material configured to initiate combustion of the air-fuel mixture to produce combustion products. The second micro-hotplate is further configured to measure a heat of combustion of the air-fuel mixture. A sensor exhaust is in flow communication with the sensor and configured to measure a volumetric flow rate of the combustion products.

DETAILED DESCRIPTION OF THE INVENTION

The present invention provides a method, sensor and system for measuring a lower heating value (LHV) and a Wobbe Index for a gaseous fuel. While the methods and systems are herein described in the context of a gas turbine engine used in an industrial environment, it is contemplated that the method and system described herein may find utility in other combustion system applications. In addition, the principles and teachings set forth herein are applicable to gas turbine engines using a variety of combustible fuels, such as natural gas, gasoline, kerosene, diesel fuel and jet fuel. The description hereinbelow is therefore set forth only by way of illustration rather than limitation.

Figure 1:
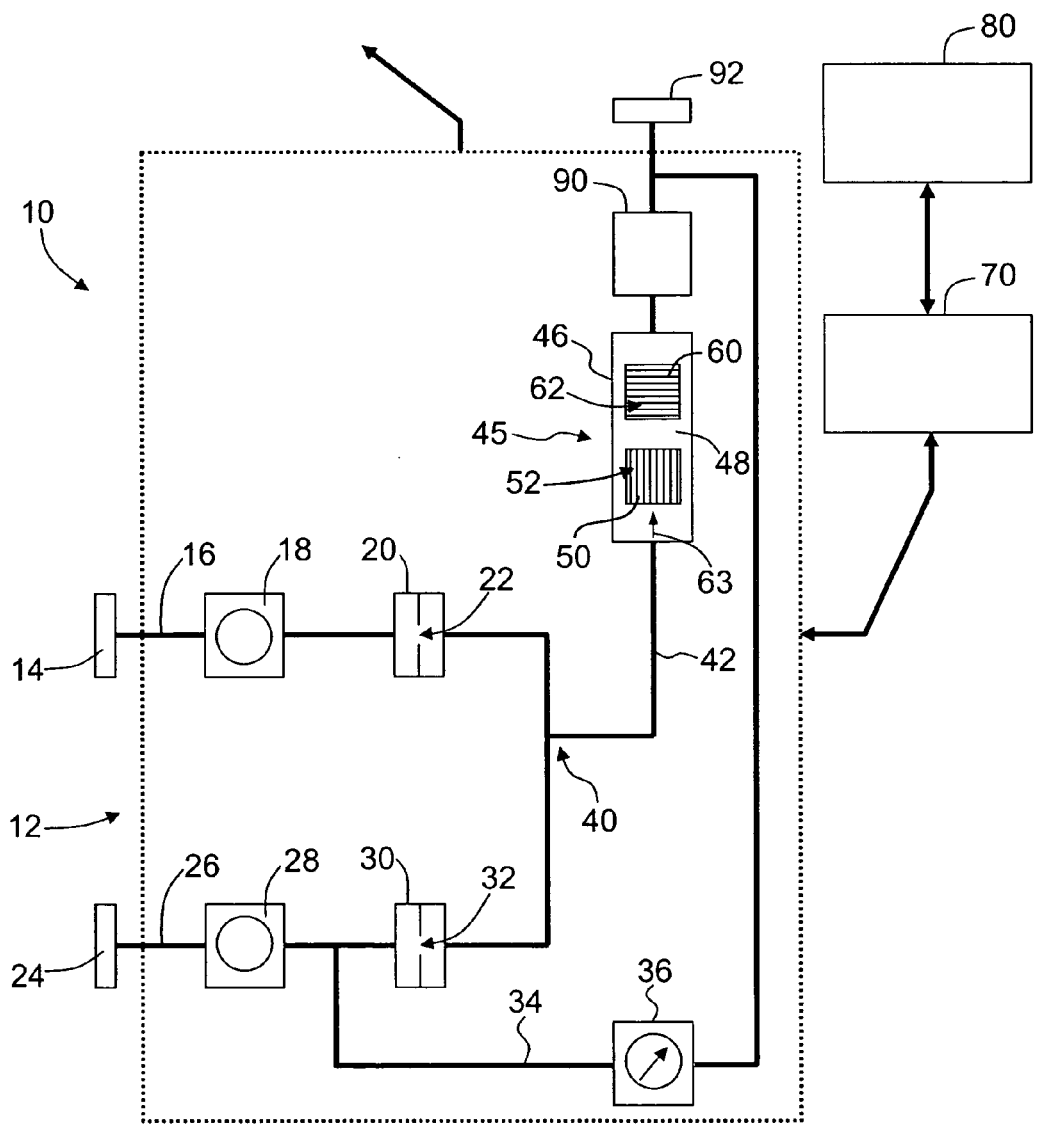
FIG. 1 is a schematic view of a system for measuring a lower heating value and/or a Wobbe Index for a gaseous fuel.
Figure 2:
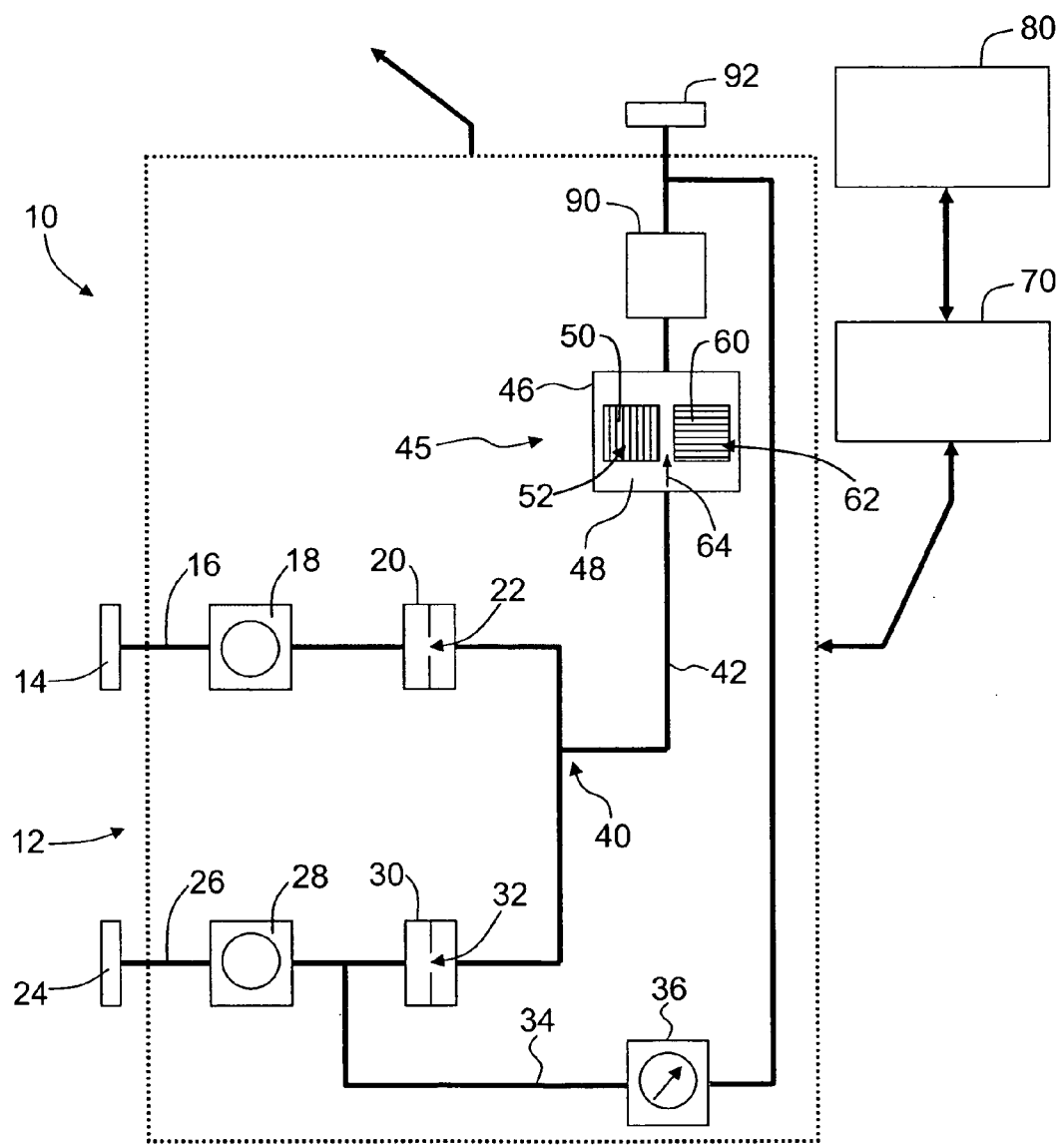
FIG. 2 is a schematic view of an alternative system for measuring a lower heating value and/or a Wobbe Index for a gaseous fuel.

Referring to FIGS. 1 and 2, a system 10 for measuring a lower heating value and a Wobbe Index of a gaseous fuel includes a flow control device 12 that controls a flow rate of a mixture of combustible fuel and air hereinafter referred to as "air-fuel mixture." In one embodiment, proportions of air to fuel are fixed such that the equivalence ratio, $\Phi$, is less than 1 (lean flow mixture). Flow control device 12 includes at least one air inlet 14 that directs a supply of air through an air supply line 16. A pressure regulator 18 regulates the pressure of air through flow control device 12. An orifice plate 20 defines an orifice 22 in flow communication with regulator 18. A backing pressure through orifice 22 is adjusted using pressure regulator 18 such that the air flow through orifice 22 is choked. With the pressure upstream of orifice 22 sufficiently higher than the pressure downstream, the velocity of the air flowing through orifice 22 will be substantially constant. This flow is referred to as a "choked" flow. By maintaining a choked air flow condition, the mass flow of the air is kept substantially stable when compared to an unchoked air flow.

Similarly, a supply of gaseous fuel, such as natural gas, is directed through at least one fuel inlet 24 and through a fuel supply line 26. A pressure regulator 28 regulates the pressure of gaseous fuel through flow control device 12. An orifice plate 30 forms an orifice 32 in flow communication with regulator 28. A backing pressure through orifice 32 is adjusted using pressure regulator 28 such that the gaseous fuel flow through orifice 32 is choked. With the pressure upstream of orifice 32 sufficiently higher than the pressure downstream, the velocity of the gaseous fuel flowing through orifice 32 will be substantially constant, e.g., a "choked" flow. By maintaining a choked gaseous fuel flow condition, the mass flow of the gaseous fuel is kept substantially stable when compared to an unchoked gaseous fuel flow. It is possible to have changes in mass flow if the density of the gaseous fuel changes. However, the variation in mass flow is easily calculated given a density of the gaseous fuel and the choked flow.

Flow control device 12 and, more specifically, pressure regulator 28 is configured to control the mass flow of gaseous fuel to balance the mass flow of gaseous fuel with the mass flow of air from air supply line 16 to achieve a selected air to fuel ratio. Additionally or alternatively, pressure regulator 18 is configured to control the mass flow of air to balance the mass flow of air with the mass flow of gaseous fuel from fuel supply line 26 to achieve a selected air to fuel ratio. Additionally, flow control device 12 is suitable to control the flow of high temperature fuels having a temperature up to at least about 200° C., and using filters fuels with contaminants, such as particulates and tars.

In one embodiment, a bypass 34 is in flow communication with fuel supply line 26. Bypass 34 is operatively controlled by a variable needle valve 36 to provide or allow an increased fuel flowrate through bypass 34 to supply a suitable amount of fuel to a sensor positioned downstream, as desired. For example, orifice 32 may control the fuel flow through fuel supply line 26 down to a small value such that a sensor response time is undesirably increased due to the overall distance between fuel inlet 24 and the sensor positioned downstream. To decrease the sensor response time, variable needle valve 36 is activated to open and provide an increased fuel flow through bypass 34 to supply a suitable amount of fuel to the sensor.

The supply of air and the supply of fuel are combined and mixed at a piping junction 40. A main air-fuel supply line 42 is in flow communication with each of air supply line 16 and fuel supply line 26 at piping junction 40. In one embodiment, a percentage of air and/or a percentage of a gaseous fuel for the air-fuel mixture is selected such that the air-fuel mixture is combustible. Main air-fuel supply line 42 directs the air-fuel mixture through a sensor 45 in flow communication with main air-fuel supply line 42. In one embodiment, sensor 45 includes an enclosure 46 that defines a chamber 48 therein.

Sensor 45 includes a first or reference micro-hotplate 50 and a second or catalyst micro-hotplate 60 positioned with respect to reference micro-hotplate 50. As shown in FIGS. 1 and 2, reference micro-hotplate 50 and catalyst micro-hotplate 60 are positioned within chamber 48. In one embodiment, reference micro-hotplate 50 is aligned in series with catalyst micro-hotplate 60 with respect to a direction of air-fuel mixture flow through chamber 48, as shown by directional arrow 63 in FIG. 1. In an alternative embodiment, reference micro-hotplate 50 is aligned in parallel with catalyst micro-hotplate 60 with respect to a direction of air-fuel mixture flow through chamber 48, as shown by directional arrow 64 in FIG. 2. As shown in FIGS. 1 and 2, two micro-hotplates, e.g., reference micro-hotplate 50 and catalyst micro-hotplate 60, are shown for simplicity. However, sensor 45 can include any suitable number of reference micro-hotplates 50 and/or catalyst micro-hotplates 60 to increase the combustion conversion efficiency. It is apparent to those skilled in the art and guided by the teachings herein provided that any suitable number of reference micro-hotplates 50 and/or catalyst micro-hotplates 60 can be used in parallel and/or in series with respect to the direction of air-fuel mixture flow within chamber 48.

Referring to FIG. 1, in one embodiment, reference micro-hotplate 50 includes a silicon nitride membrane suspended from a frame of silicon. The reference micro-hotplate 50 is fabricated from an alumina material. In alternative embodiments, reference micro-hotplate 50 is fabricated from any suitable material known to those skilled in the art and guided by the teachings herein provided. As the air-fuel mixture flows across a flow surface 52 of micro-hotplate 50, heat from reference micro-hotplate 50 is transferred to the air-fuel mixture.

The air-fuel mixture then flows across catalyst micro-hotplate 60. In one embodiment, catalyst micro-hotplate 60 includes a silicon nitride membrane suspended from a frame of silicon. At least a portion of catalyst micro-hotplate 60 is coated with a catalyst. As the air-fuel mixture flows across the surface of the catalyst coating, the air-fuel mixture is initiated to combust as a result of contact with the catalyst coating, and the heat of combustion reduces the power requirement for catalyst micro-hotplate 60.

In other alternative embodiments, a supported catalyst coating material is applied to a support material of catalyst micro-hotplate 60 on flow surface 62. The particular choice of catalyst and operating temperature is dependent upon the application. The catalyst can be, for example, a noble metal, noble metals with additives (e.g., copper), semiconducting oxides and/or hexaaluminate materials. The catalyst can be supported in high-temperature-stable, high-surface-area materials, such as alumina, hexaaluminates, zirconia, ceria, titania or hydrous metal oxides (e.g., hydrous titanium oxide (HTO), silica-doped hydrous titanium oxide (HTO:Si), and silica-doped hydrous zirconium oxide (HZO:Si)). These supported catalysts have good stability and reactivity and help to mitigate against reliability problems and failure modes by insulating catalyst micro-hotplate 60 from the harsh combustion conditions. In one embodiment, catalyst micro-hotplate 60 includes an alumina-supported catalyst including a noble metal, such as Pt or Pd, supported in an alumina matrix.

The supported catalyst can be deposited on flow surface 62 of catalyst micro-hotplate 60 that is exposed to the flow of the air-fuel mixture. In one embodiment, the catalyst is thick enough to provide sufficient catalytic activity, but thin enough to allow for adequate heat transfer between the micro-hotplate surface and the catalyst surface in contact with gases to be combusted. Reliable deposition of catalysts is desirable in order to achieve consistent performance. The catalysts are deposited onto flow surface 62 of catalyst micro-hotplate 60 using any suitable process known in the art and guided by the teachings herein provided.

Other suitable materials for fabricating reference micro-hotplate 50 and/or catalyst micro-hotplate 60 are disclosed in U.S. Pat. No. 6,786,716 issued to Gardner, et al. on Sep. 7, 2004, the disclosure of which is incorporated herein in its entirety by reference thereto. In other alternative embodiments, reference micro-hotplate 50 and/or catalyst micro-hotplate 60 include any suitable support material and/or coating material known to those skilled in the art and guided by the teachings herein provided.

A temperature control circuit 70 is in operational control communication with reference micro-hotplate 50 and/or catalyst micro-hotplate 60. Temperature control circuit 70 maintains reference micro-hotplate 50 and/or catalyst micro-hotplate 60 at a substantially constant temperature. Temperature control circuit 70 facilitates active control of reference micro-hotplate 50 and/or catalyst micro-hotplate 60 by varying the power to reference micro-hotplate 50 and/or catalyst micro-hotplate 60 to maintain a set resistance, and therefore a set temperature.

In one embodiment, temperature control circuit 70 measures the power (via current and/or voltage) required to maintain reference micro-hotplate 50 and/or catalyst micro-hotplate 60 at a substantially constant temperature. For example, heat from reference micro-hotplate 50 is transferred to the air-fuel mixture and by monitoring the change in power supplied to micro-hotplate 50 required to maintain micro-hotplate 50 at a substantially constant temperature a convective and conductive power loss is measurable. Further, when external heating from combustion attempts to increase the temperature of flow surface 62, the circuit power decreases to compensate. Thus, temperature control circuit 70 maintains catalyst micro-hotplate 60 at a substantially constant temperature. In one embodiment, a computer 80 is interfaced with temperature control circuit 70 to monitor and/or record measurements taken within sensor 45. An energy content of the gaseous fuel is obtained by combining the measured convective and conductive heat loss from reference micro-hotplate 50 and the measured heat release during the combustion of the air-fuel mixture as the air-fuel mixture flows across catalyst micro-hotplate 60.

The overall change in the power supplied to reference micro-hotplate 50 and/or catalyst micro-hotplate 60 is a directly related to the LHV. The time response of reference micro-hotplate 50 and/or catalyst micro-hotplate 60 is on the order of milliseconds. As a result, the LHV is measured in real time. Further, by measuring the change in power due to convective and conductive power losses and the change in power due to heat release, the energy content of the fuel ($\Delta$Power) is determined. If 100% combustion takes place, a direct measurement of the LHV is obtained. With a combustion conversion efficiency of less than 100%, a calibration is applied to determine the LHV.

The combustion products resulting from the combustion of the air-fuel mixture within sensor 45 are directed through a sensor exhaust 90 before being exhausted to the atmosphere through exhaust outlet 92. Sensor exhaust 90 serves as a feedback device with flow control system 12 such that flow control system 12 can correct for a small variation in mass flow across reference micro-hotplate 50 and/or catalyst micro-hotplate 60. In one embodiment, sensor exhaust 90 is in communication with computer 80. With a measurement of the mass flow value and the energy content, the LHV and the Wobbe Index of the fuel is computed with computer 80. In contrast to conventional GC system measurements which are calculated and noncontinuous, sensor 45 provides a direct and continuous measurement of the LHV and the Wobbe Index. Further, sensor 45 is relatively inexpensive when compared to conventional GC systems. Additionally, if a known amount of fuel is completely combusted within sensor 45, an amount of heat released can be determined. This information can then be used to directly determine the LHV of the fuel. The advantage of this technique is that no a priori assumption on the fuel composition and/or correlation is required.

In one embodiment, a method for measuring a lower heating value of a gaseous fuel is provided. The method includes mixing a gaseous fuel with air to provide a combustible air-fuel mixture. The air-fuel mixture is directed to flow across flow surface 52 of reference micro-hotplate 50. A change in power supplied to reference micro-hotplate 50 due to the convective and conductive heat transfer is required to maintain a constant temperature. The change in power supplied to reference micro-hotplate is registered by temperature control circuit 70. Temperature control circuit 70 maintains flow surface 52 at a substantially constant temperature.

The air-fuel mixture is directed to flow across flow surface 62 of catalyst micro-hotplate 60. The air-fuel mixture is combusted as the air-fuel mixture flows across flow surface 62. A change in power supplied to catalyst micro-hotplate 60 due to the combustion of the air-fuel mixture is required to maintain a constant temperature. The change in power supplied to catalyst micro-hotplate 60 is registered by temperature control circuit 70. Temperature control circuit 70 maintains flow surface 62 at a substantially constant temperature.

At least one of a flow rate of air and a flow rate of the gaseous fuel is regulated to control an air to fuel ratio of the air-fuel mixture. In one embodiment, a total change in power supplied to reference micro-hotplate 50 and catalyst micro-hotplate 60 is determined and the lower heating value of the gaseous fuel is measured. Further, with the measured lower heating value and a mass flow rate measurement, a Wobbe Index of the gaseous fuel is determined.

The above-described method and system facilitate a cost-effective, accurate and continuous online measurement of the lower heating value for a gaseous fuel. More specifically, the method and system facilitate a continuous reading of the lower heating value, whereas conventional GC systems are only capable of producing a single reading once every several minutes. As a result, a lower heating value for a gaseous fuel can be reliably and efficiently determined.

Exemplary embodiments of a method and system for measuring a lower heating value for a gaseous fuel are described above in detail. The method and/or system is not limited to the specific embodiments described herein, but rather, steps of the method and/or components of the system may be utilized independently and separately from other steps and/or components described herein. Further, the described method steps and/or system components can also be defined in, or used in combination with, other methods and/or systems, and are not limited to practice with only the method and system as described herein.

While the invention has been described in terms of various specific embodiments, those skilled in the art will recognize that the invention can be practiced with modification within the spirit and scope of the claims.

What is claimed is:

1. A method for measuring a lower heating value of a gaseous fuel, said method comprising:
   mixing a gaseous fuel with air to provide a combustible air-fuel mixture;
   directing the air-fuel mixture to flow across a flow surface of a first micro-hotplate maintained at a constant temperature;
   measuring a change in power required to maintain a constant temperature of the first micro-hotplate flow surface due to a convective and conductive heat transfer from the first micro-hotplate flow surface to the air-fuel mixture;
   directing the air-fuel mixture to flow across a flow surface of a second micro-hotplate maintained at a constant temperature;
   combusting the air-fuel mixture as the air-fuel mixture flows across the second micro-hotplate flow surface; and
   measuring a change in power required to maintain a constant temperature of the second micro-hotplate flow surface due to the combustion of the air-fuel mixture.

2. A method in accordance with claim 1 wherein maintaining a constant temperature of the first micro-hotplate flow surface further comprises changing the power supplied to the first micro-hotplate due to the convective and conductive heat transfer.

3. A method in accordance with claim 1 wherein maintaining a constant temperature of the second micro-hotplate flow surface further comprises changing the power supplied to the second micro-hotplate due to the combustion of the air-fuel mixture.

4. A method in accordance with claim 1 further comprising determining a total change in power supplied to the first micro-hotplate and the second micro-hotplate to measure the lower heating value of the gaseous fuel.

5. A method in accordance with claim 4 further comprising measuring the lower heating value and a mass flow rate to measure a Wobbe Index of the gaseous fuel.

6. A method in accordance with claim 1 further comprising maintaining each of the first micro-hotplate flow surface and the second micro-hotplate flow surface at a substantially constant temperature.

7. A method in accordance with claim 6 wherein maintaining each of the first micro-hotplate flow surface and the second micro-hotplate flow surface at a substantially constant temperature further comprises coupling a temperature control circuit to each of the first micro-hotplate and the second micro-hotplate, the temperature control circuit in operational control communication with each of the first micro-hotplate and the second micro-hotplate to control a temperature of each of the first micro-hotplate flow surface and the second micro-hotplate flow surface.

8. A method in accordance with claim 1 further comprising regulating at least one of a flow rate of air and a flow rate of the gaseous fuel to control an air to fuel ratio of the air-fuel mixture.

9. A method in accordance with claim 8 wherein regulating at least one of a flow rate of air and a flow rate of the gaseous fuel further comprises correcting for changes in a volumetric flow of combustion products at a sensor exhaust.

10. A sensor for measuring a lower heating value of a gaseous fuel, said sensor comprising:
    an enclosure defining a chamber, said chamber in flow communication with an air-fuel mixture supply line configured to supply a combustible air-fuel mixture to said chamber;
    a first micro-hotplate positioned within said chamber and comprising at least one flow surface, said at least one flow surface configured to contact the air-fuel mixture flowing through said chamber; and
    a second micro-hotplate positioned within said chamber and with respect to said first micro-hotplate, said second micro-hotplate comprising at least one flow surface coated with a catalytic coating material configured to initiate a combustion of the air-fuel mixture; and
    a sensor exhaust in flow communication with said chamber.

11. A sensor in accordance with claim 10 wherein said first micro-hotplate is configured to measure a change in power required to maintain a substantially constant temperature due to convective and conductive heat loss from said first micro-hotplate to the air-fuel mixture and said second micro-hotplate is configured to measure a change in power required to maintain a substantially constant temperature due to the combustion of the air-fuel mixture.

12. A sensor in accordance with claim 10 wherein said first micro-hotplate is aligned in series with said second micro-hotplate with respect to a direction of flow of the air-fuel mixture.

13. A sensor in accordance with claim 10 wherein said first micro-hotplate is aligned in parallel with said second micro-hotplate with respect to a direction of flow of the air-fuel mixture.

14. A sensor in accordance with claim 10 further comprising a temperature control circuit in operational control communication with each of said first micro-hotplate and said second micro-hotplate, said temperature control circuit configured to maintain said first micro-hotplate and said second micro-hotplate at a substantially constant temperature.

15. A sensor in accordance with claim 14 wherein said temperature control circuit is configured to change the power supplied to each of said first micro-hotplate and said second micro-hotplate to maintain the substantially constant temperature.

16. A system for measuring a lower heating value of a gaseous fuel, said system comprising:
    a flow control device configured to control at least one of a flow rate of air and a flow rate of a gaseous fuel for providing a combustible air-fuel mixture;
    a sensor in flow communication with said flow control device, said sensor comprising:
      a first micro-hotplate including at least one flow surface, said first micro-hotplate configured to measure convective and conductive heat losses from said first micro-hotplate to the air-fuel mixture flowing across said at least one flow surface; and
      a second micro-hotplate positioned with respect to said first micro-hotplate, said second micro-hotplate comprising at least one flow surface coated with a catalytic coating material configured to initiate a combustion of the air-fuel mixture to produce combustion products, said second micro-hotplate further configured to measure a heat of combustion of the air-fuel mixture; and
    a sensor exhaust in flow communication with said sensor and configured to measure a volumetric flow rate of the combustion products.

17. A system in accordance with claim 16 wherein said flow control device further comprises:
   an air supply line;
   a first pressure regulator in flow communication with said air supply line and configured to control a pressure of air;
   a first orifice plate defining a first orifice providing flow communication between said air supply line and a air-fuel mixture line, said first orifice configured to provide a choked flow of air to said air-fuel mixture supply line;
   a gaseous fuel supply line;
   a second pressure regulator in flow communication with said gaseous fuel and configured to control a pressure of gaseous fuel; and
   a second orifice plate defining a second orifice providing flow communication between said gaseous fuel supply line and said air-fuel mixture supply line, said second orifice configured to provide a choked flow of gaseous fuel to said air-fuel mixture supply line.

18. A system in accordance with claim 16 further comprising a temperature control circuit in operational control communication with each of said first micro-hotplate and said second micro-hotplate, said temperature control circuit maintaining said first micro-hotplate and said second micro-hotplate at a substantially constant temperature.

19. A system in accordance with claim 16 wherein said flow control device further comprises:
   a first orifice plate defining a first orifice providing flow communication between an air supply line and an air-fuel mixture supply line, said first orifice configured to provide a choked flow of air to said air-fuel mixture supply line; and
   a second orifice plate defining a second orifice providing flow communication between a gaseous fuel supply line and said air-fuel mixture supply line, said second orifice configured to provide a choked flow of gaseous fuel to said air-fuel mixture supply line.

* * * * *

UNITED STATES PATENT AND TRADEMARK OFFICE
CERTIFICATE OF CORRECTION

PATENT NO. : 8,486,710 B2
APPLICATION NO. : 11/299588
DATED : July 16, 2013
INVENTOR(S) : Antel et al.

Page 1 of 1

It is certified that error appears in the above-identified patent and that said Letters Patent is hereby corrected as shown below:

On the Title Page, in Item (73), under "Assignee", in Column 1, Line 2, delete "Nisakayuna," and insert -- Niskayuna, --, therefor.

In the Specifications:

In Column 1, Line 17, delete "DE-FC26-63NT41448." and insert -- DE-FC26-03NT41448. --, therefor.

In the Claims:

In Column 9, Lines 7-8, in Claim 17, delete "a air-fuel" and insert -- an air-fuel --, therefor.

Signed and Sealed this
Third Day of September, 2013

Teresa Stanek Rea
*Acting Director of the United States Patent and Trademark Office*